United States Patent [19]

Katayama et al.

[11] Patent Number: 5,464,828

[45] Date of Patent: Nov. 7, 1995

[54] AQUEOUS SUSPENSION OF SUCRALFATE

[75] Inventors: Masahide Katayama; Harushige Yamashita; Taizo Okada; Shigeo Morioka, all of Shinagawa, Japan

[73] Assignees: Chugai Pharmaceutical Co., Ltd.; Sato Pharmaceutical Co., Ltd., both of Tokyo, Japan

[21] Appl. No.: 185,157

[22] Filed: Jan. 24, 1994

Related U.S. Application Data

[63] Continuation of Ser. No. 968,469, Oct. 29, 1992, abandoned, which is a continuation-in-part of Ser. No. 670,109, Mar. 12, 1991, abandoned, which is a continuation of Ser. No. 318,205, Mar. 2, 1989, abandoned.

[30] Foreign Application Priority Data

Mar. 2, 1988 [JP] Japan .................................. 63-47423

[51] Int. Cl.⁶ ..................................................... A61K 31/70
[52] U.S. Cl. .................................. 514/60; 514/53; 514/54
[58] Field of Search .................................. 514/53, 54, 60

[56] References Cited

U.S. PATENT DOCUMENTS 3,876,766  4/1975  Frommer et al. .......................... 514/54
4,717,713  1/1988  Zatz et al. ................................. 514/57
4,885,281  12/1989  Hanstein et al. .......................... 514/53

OTHER PUBLICATIONS

Hanstein et al, *Sucralfate Suspensions*, Chemical Abstracts, vol. 104 (1986) No. 230453v.

*Primary Examiner*—Douglas W. Robinson
*Assistant Examiner*—Elli Peselev
*Attorney, Agent, or Firm*—Sughrue, Mion, Zinn, Macpeak & Seas

[57] ABSTRACT

The invention is an aqueous suspension of sucralfate (sucrose sulfate aluminum salt), which is added with a starch and/or a derivative thereof and preferably further with a cellulose derivative, polysaccharide gum, alginic acid, alginate and/or bentonite, whereby the suspension is made stable for a long time and may be redispersed if necessary. The invention can thus provide a liquid pharmaceutical preparation useful for protecting ulcer areas on mucous membranes of the stomach and duodenum industrially for the first time, although solid pharmaceutical preparations have been available.

2 Claims, No Drawings

5,464,828

AQUEOUS SUSPENSION OF SUCRALFATE

This is a Continuation of prior parent application Ser. No. 07/968,469 filed on Oct. 29, 1992, abandoned, which is a continuation-in-part of prior application Ser. No. 07/670,109 filed Mar. 12, 1991 (abandoned), which in turn is a continuation of prior application Ser. No. 07/318,205 filed Mar. 2, 1989 (abandoned).

BACKGROUND OF THE INVENTION AND RELATED ART

The invention relates to a suspension containing sucralfate (sucrose sulfate aluminum salt) as a pharmaceutically effective component.

The sucralfate can combine directly with pepsin in gastric juice to suppress the activity thereof. It has antipepsin and antiacid effects. The sucralfate can form a covering film over mucous membranes of the stomach and duodenum to protect the membrane. This effect is to selectively couple with an ulcer area of the digestive tract for the protection of the diseased part.

Pharmaceutical preparations containing this sucralfate have been provided in the solid form such as tablets, granules, pellets or powders. Since the sucralfate is not water soluble, the liquid form of the preparation must be a suspension but any of the usual assistants cannot hold the suspension stable for a long time.

JP-A 503031/1986 discloses a suspension containing sucralfate, to which 1–5 weight % of xanthan gum and 1–12.5 weight % of at least one peptizer are added. This is not satisfactory, however, in that it is necessary to control the particle dimension of sucralfate to be smaller than 50 μm since if the particle dimension is larger than that the suspension is unstable due to particle sedimentation. Since the amount referred to above of xanthan gum is to be added is in relation to sucralfate, the viscosity of the suspension is too low when the sucralfate content therein is fairly small. It is necessary in this case to add glycerin or the like in order to increase the viscosity. In the case where sucralfate is added in a considerable amount in the suspension, this gives a slurry rather than the suspension so as to be difficult to take.

Meanwhile, it is well Known that solid pharmaceutical preparations generally necessitate a considerably long time until the preparations are disintegrated and consequently until the medicinal effect appears, different from liquid pharmaceutical preparations.

In order to prepare an aqueous suspension, it is well known to generally use a dispersing agent such as acacia, carboxy methyl cellulose sodium, hydroxypropyl methyl cellulose, hydroxyethyl cellulose, crystalline cellulose, alginate, gelatin and bentonite.

Since sucralfate produces $A^{3+}$ ions in an aqueous medium so as to cause mutual reaction with such dispersing agent, sucralfate particles are bound together to cause rapid sedimentation, whereby the suspension cannot be redispersed or is changed to be in a semi-solid state due to gelation of the dispersing agent under the influence of such ions.

There is a possibility depending on the kind of the dispersing agents that the dispersed phase tends to cause sedimentation gradually from particles of larger dimension and higher density. In the course of a so-called free sedimentation for a long time, agglomeration is formed in the suspension (caking phenomenon) so that even if strongly shaken it is impossible to redisperse. It is necessary for the suspension that not only sedimentation of the dispersed phase is retarded as far as possible but also redispersion can be readily made.

SUMMARY OF THE INVENTION

It is an object of the invention, thus, to provide a stable and readily redispersable aqueous suspension of sucralfate.

It is another object is to manufacture a pharmaceutical preparation in the form of the aqueous suspension referred to above readily and without any considerable additional expense.

The other objects of the invention and advantages attained thereby are appreciated by those skilled in the art when studying following explanation of the invention in more detail.

DESCRIPTION OF THE PREFERRED EMBODIMENTS OF THE INVENTION

The inventors have devoted themselves to various experiments to find out that combining a starch and/or a derivative thereof with an aqueous suspension of sucralfate to form a sort of network structure interacted among particles thereof can provide a stable and readily redispersable suspension, and that when further adding at least one material selected from a group consisting of cellulose derivatives, polysaccharide gums, alginic acid salts and bentonite, a more preferable aqueous suspension can be obtained, which is stable for a long time even if it contains sucralfate particles each of which is on the order of 100 μm.

The dispersing agent to be used in the invention is a starch and/or a derivative thereof. The starch may be any of those of wheat, potate, rice, glutinous rice, maize or corn and glutinous maize or corn. As for the starch derivative, there are starch esters such as acetate, succinate, nitrate, phosphate and xanthate; starch ethers such as allyl ether, methyl ether, carboxymethyl ether, hydroxyethyl ether, hydroxypropyl ether and cationic search; and cross-linked starches such as formaldehyde-, epichlorohydrin- and phosphoric acid-crosslinked starches.

The cellulose derivative added in the suspension in addition to the starch and/or the derivative thereof is a cellulose ether such as methyl cellulose, ethyl cellulose, benzyl cellulose, carboxymethyl cellulose, carboxylethyl cellulose, sodium carboxymethyl cellulose, hydroxyethyl cellulose, hydroxypropyl cellulose and hydroxypropylmethyl cellulose; a polysaccharide gum such as acacia, tragacanth gum, karaya gum, guar gum, quince seed, carrageenan, locust bean gum, tamarind gum and dextran; or an alginic acid salt such as alginic acid, sodium alginate and propylene glycol alginate.

In relation to the total amount of the sucralfate suspension, generally added are sucralfate in the amount of 0.1–50 w/v %, preferably 0.5–20 w/v %, the starch and/or the starch derivative in the amount of 0.05–10.0 w/v %, preferably 0.1–5.0 w/v %, and the further additive(s) such as the cellulose derivatives, polysaccharide gums and bentonite in the amount of 0.05–5.0 w/v %, preferably 0.1–2.0 w/v %.

The sucralfate suspension according to the invention may comprise, as occasion demands, further an adsorbent such as kaolin and natural aluminum silicate; an antiseptic such as sodium benzoate, ethyl para-hydroxybenzoate, methyl para-hydroxybenzoate, propyl para-hydroxybenzoate, butyl para-hydroxybenzoate, dehydroacetic acid and a salt thereof; a defoaming agent such as silicone resin; a flavour and a colouring agent such as purified sucrose, glucose and D-sorbitol; an inorganic antiacid such as magnesium aluminosilicate, synthetic aluminum silicate, dried aluminum hydroxide gel and synthetic hydrotalcite; an amino acid such as aminoacetic acid and dihydroxyaluminum aminoacetate; a stomachic crude drug such as aloe, cinnamon bark, magnolia bark, ginger and ginseng; a cholagogous such as ursodeoxycholic, dehydrocholic acid and powdered bile; an intestinal ordering crude material such as geranium herb; an analgesic anodyne and anti-spamodic such as corydalis tuber and glycyrrhiza; and a covering agent such as precipitated calcium carbonate and calcium hydrogenphosphate.

The invention will be explained in more detail in reference to some Examples. It is noted that the invention is not restricted thereto.

| Example 1 | |
|---|---|
| Prescription; | |
| Sucralfate | 1.5 g |
| Magnesium aluminometasilicate | 1.5 g |
| Maize starch | 0.5 g |
| Hydroxypropyl starch | 3.0 g |
| Purified sucrose | 10.0 g |
| Sodium benzoate | 0.05 g |
| Disodium acetate | 0.01 g |
| Ethanol | 1.0 g |
| Flavour | very small quantity |
| Purified water added to be totally | 100.0 ml |

Firstly sucralfate and magnesium aluminometasilicate are weighed and added with 30 ml pure water to be stirred until a homogeneous phase is caused. Separately, maize starch and hydroxypropyl starch are weighed, and added with 40 ml purified water to be stirred with heating. Said two mixtures are vigorously stirred to be homegenous, to which purified sucrose, sodium benzoate, disodium acetate, ethanol and flavour are added to be dissolved and further added with purified water so as to make the total amount to be 100 ml. In following Examples 2–4, the aqueous suspensions were prepared similar to the above.

| Example 2 | |
|---|---|
| Sucralfate | 2.0 g |
| Hydroxypropyl starch | 3.0 g |
| Hydroxypropyl cellulose | 1.0 g |
| Purified sucrose | 10.0 g |
| Sodium benzoate | 0.05 g |
| Purified water added to be totally | 100.0 ml |
| Example 3 | |
| Sucralfate | 3.0 g |
| Maize starch | 2.0 g |
| Pulverized tragacanth gum | 0.8 g |

-continued

| | |
|---|---|
| Purified sucrose | 10.0 g |
| Sodium benzoate | 0.05 g |
| Purified water added to be totally | 100.0 ml |
| Example 4 | |
| Sucralfate | 4.0 g |
| Hxdroxypropyl starch | 1.5 g |
| Propylene glycol alginate | 0.3 g |
| Purified sucrose | 10.0 g |
| Sodium benzoate | 0.05 g |
| Purified water added to be totally | 100.0 ml |
| Example 5 | |
| Sucralfate | 7.0 g |
| Maize starch | 1.0 g |
| Bentonite | 0.8 g |
| Purified sucrose | 10.0 g |
| Sodium benzoate | 0.05 g |
| Purified water added to be totally | 100.0 ml |

As controls, the following four aqueous suspensions were prepared.

| Comparative Example 1 | |
|---|---|
| Sucralfate | 1.0 g |
| Hydroxypropyl cellulose | 1.0 g |
| Purified sucrose | 10.0 g |
| Sodium benzoate | 0.05 g |
| Purified water added to be totally | 100.0 ml |
| Comparative Example 2 | |
| Sucralfate | 2.0 g |
| Carrageenan | 1.0 g |
| Purified sucrose | 10.0 g |
| Sodium benzoate | 0.05 g |
| Purified water added to be totally | 100.0 ml |
| Comparative Example 3 | |
| Sucralfate | 2.0 g |
| Sodium carboxymethyl cellulose | 1.0 g |
| Purified sucrose | 10.0 g |
| Sodium benzoate | 0.05 g |
| Purified water added to be totally | 100.0 ml |
| Comparative Example 4 | |
| Sucralfate | 1.0 g |
| Xanthane gum | 0.02 g |
| $NaH_2PO_4$ | 0.03 g |
| Purified sucrose | 10.0 g |
| Sodium benzoate | 0.05 g |
| Purified water added to be totally | 100.0 ml |

Preparations of Examples 1, 3 and 5 as well as Comparative Examples 1–4 were stored at temperatures of 3° C., 20° C. and 40° C. respectively for 3 months to examine the stability, results of which are as follows;

| | Immediately After Preparation | After 3 Months (At 3° C.) | After 3 Months (At 20° C.) | After 3 Months (At 40° C.) |
|---|---|---|---|---|
| Example 1 | Stable | Stable | Stable | Stable |
| Example 3 | Stable | Stable | Stable | Stable |
| Example 5 | Stable | Stable | Stable | Slight Sedimentation |
| Comparative Example 1 | Stable | Not Stable (Caking) | Not Stable (Caking) | Not Stable (Caking) |
| Comparative Example 2 | Stable | Not Stable (Gelation) | Not Stable (Gelation) | Not Stable (Gelation and Caking) |

|  | Immediately After Preparation | After 3 Months (At 3° C.) | After 3 Months (At 20° C.) | After 3 Months (At 40° C.) |
| --- | --- | --- | --- | --- |
| Comparative Example 3 | Not Stable (Gelation) | Not Stable (Gelation) | Not Stable (Gelation) | Not Stable (Gelation) |
| Comparative Example 4 | Stable | Not Stable (Caking) | Not Stable (Caking) | Not Stable (Caking) |

In following Comparative Example 5 and Examples 6–12, the aqueous suspensions were prepared similar to the procedure used in Example 1.

| | Comparative Example 5 | Example 6 | Example 7 | Example 8 | Example 9 | Example 10 | Example 11 | Example 12 |
| --- | --- | --- | --- | --- | --- | --- | --- | --- |
| | | | | (unit:g) | | | | |
| Sucralfate | 5.0 | 5.0 | 5.0 | 5.0 | 5.0 | 5.0 | 10.0 | 2.0 |
| H.P.S. *1 | — | 1.0 | — | — | 0.5 | 2.0 | 3.5 | 0.5 |
| Maize starch | — | — | 2.0 | — | — | — | — | — |
| Potato Starch | — | — | — | 1.5 | — | — | — | 1.0 |
| H.P.C. *2 | — | — | — | — | 2.0 | — | — | — |
| C.M.C.-Na *3 | — | — | — | — | — | 0.05 | — | — |
| Paraben *4 | 0.1 | 0.1 | 0.1 | 0.1 | 0.1 | 0.1 | 0.1 | 0.1 |
| Purified Water Added to make | 100 ml | 100 ml | 100 ml | 100 ml | 100 ml | 100 ml | 100 ml | 100 ml |
| Condition | Precipitation | Precipitation | Precipitation | Precipitation | Precipitation | Precipitation | Good | Precipitation |
| Shaking times for obtaining redispersion *5 | about 30 times | about 5 times | about 5 times | about 3 times | about 9 times | about 4 times | about 2 times | about 5 times |

*1 Hydroxy propyl starch
*2 Hydroxy propyl cellulose
*3 Sodium carboxymethyl cellulose
*4 Methyl paraben and propyl paraben = 1:1
*5 Determination method: 50 ml of medicine is filled up into transparent glass bottle of about 38p and said bottle is shaken at a speed of 120 times/min.

After keeping these medicines as they were at room temperature for two months, the precipitation states and redispersibilities thereof were determined.

In Comparative Example 5 to which no dispersion agent was added, sucralfate was easily solidified and redispersibility was not good, while in Examples No. 6–12 to which starch and cellulose derivatives as claimed were respectively added, good redispersibility was attained with a small number of shakings.

What is claimed is:

1. An aqueous suspension consisting essentially of sucralfate and hydroxypropyl starch, wherein the sucralfate is present in an amount of 0.1–50 w/v % and the hydroxypropyl starch is present in an amount of 0.05–10.0 w/v %.

2. An aqueous suspension consisting essentially of sucralfate and hydroxypropyl starch, wherein the sucralfate is present in an amount of 0.5–20 w/v % and the hydroxypropyl starch is present in an amount of 0.1–5.0 w/v %.

* * * * *